US012601736B2

(12) United States Patent
Terry et al.

(10) Patent No.: US 12,601,736 B2
(45) Date of Patent: Apr. 14, 2026

(54) BIOMARKER DETECTION USING LAYERED RECEPTOR AND ELECTRODE CONFIGURATION

(71) Applicant: MindMend Biotech LLC, Gaithersburg, MD (US)

(72) Inventors: Mercedes Terry, Canyon, TX (US); Blair Dupre, Gaithersburg, MD (US); Abigail Tubbs, Gaithersburg, MD (US); Kiley House, Rochester, MN (US); Jude Shupe, Grand Forks, ND (US)

(73) Assignee: MindMend Biotech LLC, Gaithersburg, MD (US)

( * ) Notice: Subject to any disclaimer, the term of this patent is extended or adjusted under 35 U.S.C. 154(b) by 0 days.

(21) Appl. No.: 19/173,571

(22) Filed: Apr. 8, 2025

(65) Prior Publication Data

US 2025/0334570 A1 Oct. 30, 2025

Related U.S. Application Data

(60) Provisional application No. 63/636,248, filed on Apr. 19, 2024.

(51) Int. Cl.
*G01N 33/543* (2006.01)
*A61B 5/0537* (2021.01)
(Continued)

(52) U.S. Cl.
CPC ....... *G01N 33/5438* (2013.01); *A61B 5/0537* (2013.01); *A61B 5/1477* (2013.01); *G01N 27/128* (2013.01); *G01N 33/54346* (2013.01)

(58) Field of Classification Search
CPC .. A61B 5/0537; A61B 5/1477; G01N 27/128; G01N 33/54346; G01N 33/5438
See application file for complete search history.

(56) References Cited

U.S. PATENT DOCUMENTS

| | | | |
|---|---|---|---|
| 8,901,620 | B2 | 12/2014 | Lee et al. |
| 10,989,684 | B2 | 4/2021 | Grabbert et al. |

(Continued)

FOREIGN PATENT DOCUMENTS

| | | | |
|---|---|---|---|
| EP | 4019971 B1 | 11/2023 | |
| KR | 101170837 B1 | 8/2012 | |

(Continued)

OTHER PUBLICATIONS

Tao, Dan, et al. "Ultrasensitive detection of alpha-synuclein oligomer using a PolyD-glucosamine/gold nanoparticle/carbon-based nanomaterials modified electrochemical immunosensor in human plasma." Microchemical Journal 158 (2020): 105195. (Year: 2020).*

(Continued)

*Primary Examiner* — Robert J Eom

(57) ABSTRACT

Herein disclosed is configuring a layered receptor with at least one layer comprising graphene oxide and an biomarker binding layer configured to bind with a targeted biomarker, connecting a working electrode comprising carbon nanotubes (CNT) and a reference electrode to the layered receptor, and detecting events comprising the targeted biomarker binding layer with the biomarker binding layer, by measuring changes in impedance to a plurality of frequencies of an alternating current voltage signal applied through a patient's body fluid between the working electrode and the reference electrode. The layered receptor may further comprise a plurality of self-assembled layers, comprising, in sequence, a layer abutting the CNT and comprising a polymer and metal nanoparticles, a layer comprising an organosulfur, the graphene oxide layer and the biomarker binding layer. The biomarker binding layer may comprise Syn-211, LB509 or 5G4. The targeted biomarker may be alpha-synuclein. An (Continued)

implementation may report biomarker concentrations in real-time based on detected binding events.

17 Claims, 5 Drawing Sheets

Specification includes a Sequence Listing.

(51) Int. Cl.

| | |
|---|---|
| ***A61B 5/1477*** | (2006.01) |
| ***G01N 27/12*** | (2006.01) |

(56) References Cited

U.S. PATENT DOCUMENTS

| | | | |
|---|---|---|---|
| 11,726,086 | B2 | 8/2023 | Zhang et al. |
| 2019/0212263 | A1 | 7/2019 | Chiu et al. |
| 2019/0227082 | A1 | 7/2019 | Barbour et al. |
| 2021/0396703 | A1 | 12/2021 | Nazarian et al. |
| 2022/0196666 | A1 | 6/2022 | Abedi et al. |

FOREIGN PATENT DOCUMENTS

| | | | |
|---|---|---|---|
| KR | 101654467 | B1 | 9/2016 |
| KR | 102455729 | B1 | 10/2022 |
| WO | 2018008964 | A1 | 1/2018 |

OTHER PUBLICATIONS

Ionescu, Rodica Elena. "Use of cysteamine and glutaraldehyde chemicals for robust functionalization of substrates with protein biomarkers—an overview on the construction of biosensors with different transductions." Biosensors 12.8 (2022): 581. (Year: 2022).*

Singal, Shobhita, et al. "Immunoassay for troponin I using a glassy carbon electrode modified with a hybrid film consisting of graphene and multiwalled carbon nanotubes and decorated with platinum nanoparticles." Microchimica Acta 183.4 (2016): 1375-1384. (Year: 2016).*

Pruneanu, Stela, et al. "Electro-catalytic properties of graphene composites containing gold or silver nanoparticles." Electrochimica Acta 89 (2013): 246-252. (Year: 2013).*

* cited by examiner

BIOMARKER DETECTION USING LAYERED RECEPTOR AND ELECTRODE CONFIGURATION

CROSS-REFERENCE TO RELATED APPLICATIONS

This application claims the benefit of U.S. Provisional Patent Application No. 63/636,248, titled "BIOMARKER DETECTION USING LAYERED RECEPTOR AND ELECTRODE CONFIGURATION," filed Apr. 19, 2024 by Blair Dupre and Mercedes Terry and this application incorporates the entire contents of the above-referenced application herein by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 7207 byte XML file named "10700.0001_seq_listing.xml" created on Apr. 14, 2025.

TECHNICAL FIELD

This disclosure relates generally to bioelectrical impedance analysis using layered receptors and nanotechnology.

BACKGROUND

The ability to diagnose and monitor disease and/or disease state is a critical aspect of quality healthcare. Detection and monitoring of biomarkers in a patient can provide important information to healthcare providers. These biomarkers, which may comprise proteins, nucleic acids, or other molecules, found in a patient, and provide valuable information about the health status of an individual or the progression of a disease. The ability to detect these biomarkers accurately and efficiently can lead to early diagnosis, personalized treatment plans, and improved patient outcomes. The development and application of a biosensor that accurately detects and provides data as to level or amount of a biomarker in a patient, or sample of a patient, can be critical for disease detection and management.

Biosensors are analytical devices that combine a biological component with a physicochemical detector to detect and quantify specific substances, such as biomarkers, in a complex matrix, such as a patient's body or bodily fluids. Antibodies are proteins produced by the immune system in response to the presence of a specific antigen. These antibodies may be produced by and isolated from lab cultures. Antibodies have a high affinity and specificity for binding their target antigens, making them ideal for use in biosensors.

Electrochemical Impedance spectroscopy (EIS) is a technique that measures the electrical impedance of a system as a function of frequency. EIS has been widely used in the field of biosensing due to its label-free, non-destructive, and real-time monitoring capabilities. The impedance of a system can be affected by various factors, including the presence of biomolecules on the sensor surface. Therefore, changes in impedance can be used to detect the binding events between the target analyte and the immobilized antibodies.

Graphene, a two-dimensional carbon allotrope, has been extensively studied due to its unique properties, such as high electrical conductivity, large surface area, and biocompatibility. Graphene-based materials have been incorporated into biosensors to enhance their performance, such as improving the sensitivity and selectivity of the detection. However, the integration of these materials into a biosensor, and the development of methods for using these sensors to detect biomarkers, presents several challenges. These challenges include, but are not limited to, the stability of the materials, the efficiency of the antibody binding, and the accuracy of the impedance measurements.

Despite the advancements in the field, there remains a need for improved methods and devices for detecting biomarkers. In particular, there is a need for methods and devices that can provide accurate, reliable, real-time data, while also being easy to use and cost-effective. Therefore, there is a need for new methods and devices that can effectively address these challenges and provide improved capabilities for detecting biomarkers.

SUMMARY

Herein disclosed is an apparatus for measuring biomarkers, for example to diagnose a disease and/or detect a state of disease in a patient. The apparatus comprises a layered receptor with at least one layer comprising graphene or graphene oxide (GO), and a biomarker binding layer configured to bind with a targeted biomarker, a working electrode comprising carbon nanotubes (CNT), and a reference electrode to the layered receptor. The layered receptor may further comprise a plurality of self-assembled layers, comprising, in sequence, a layer abutting the CNT and comprising a polymer and metal nanoparticles, a layer comprising an organosulfur, the GO layer, and the biomarker binding layer. The biomarker binding layer may comprise, but not be limited to Syn-211, LB509, or 5G4. The targeted biomarker may comprise but not be limited to alpha-synuclein.

Herein disclosed is a method comprising configuring a layered receptor with at least one layer comprising graphene oxide and an biomarker binding layer configured to bind with a targeted biomarker, connecting a working electrode (WE) comprising carbon nanotubes (CNT) and a reference electrode (RE) to the layered receptor, and detecting events comprising the targeted biomarker binding layer with the targeted biomarker by measuring changes in impedance to a plurality of frequencies of an alternating current voltage signal applied through a patient's body fluid between the working electrode and the reference electrode. In this design, the CNT electrode or WE impedance is altered when due to binding events between the biomarker binding layer and the biomarker. Alternate embodiments may employ the working electrode, reference electrode, and a counter electrode (CE), wherein the CNT operates as the WE, the RE provides stable potential, and the CE balances the applied current. Yet another embodiment employs a voltage sensing electrode (SE) in addition to the WE, RE, and CE. The SE, placed near the WE, measures a voltage drop independently without drawing current. Other multi-electrode embodiments may employ more than four electrodes wherein additional SEs are employed to improve impedance resolution and spatial accuracy in which case the CNT serves as the WE, the RE provides stability, the CE completes the circuit, and one or more SEs measure impedance at different locations. The layered receptor may further comprise a plurality of self-assembled layers, comprising, in sequence: 1) a layer abutting the CNT and comprising a polymer and metal nanoparticles; 2) a layer comprising an organosulfur; 3) the graphene oxide layer; and 4) the biomarker binding layer. The biomarker binding layer may comprise, but not be limited to Syn-211, LB509, or 5G4. The targeted biomarker may comprise but not be limited to alpha-synuclein. An implementation may report biomarker concentrations in real-time based on detected binding events.

DETAILED DESCRIPTION

Terms

Figure 1:
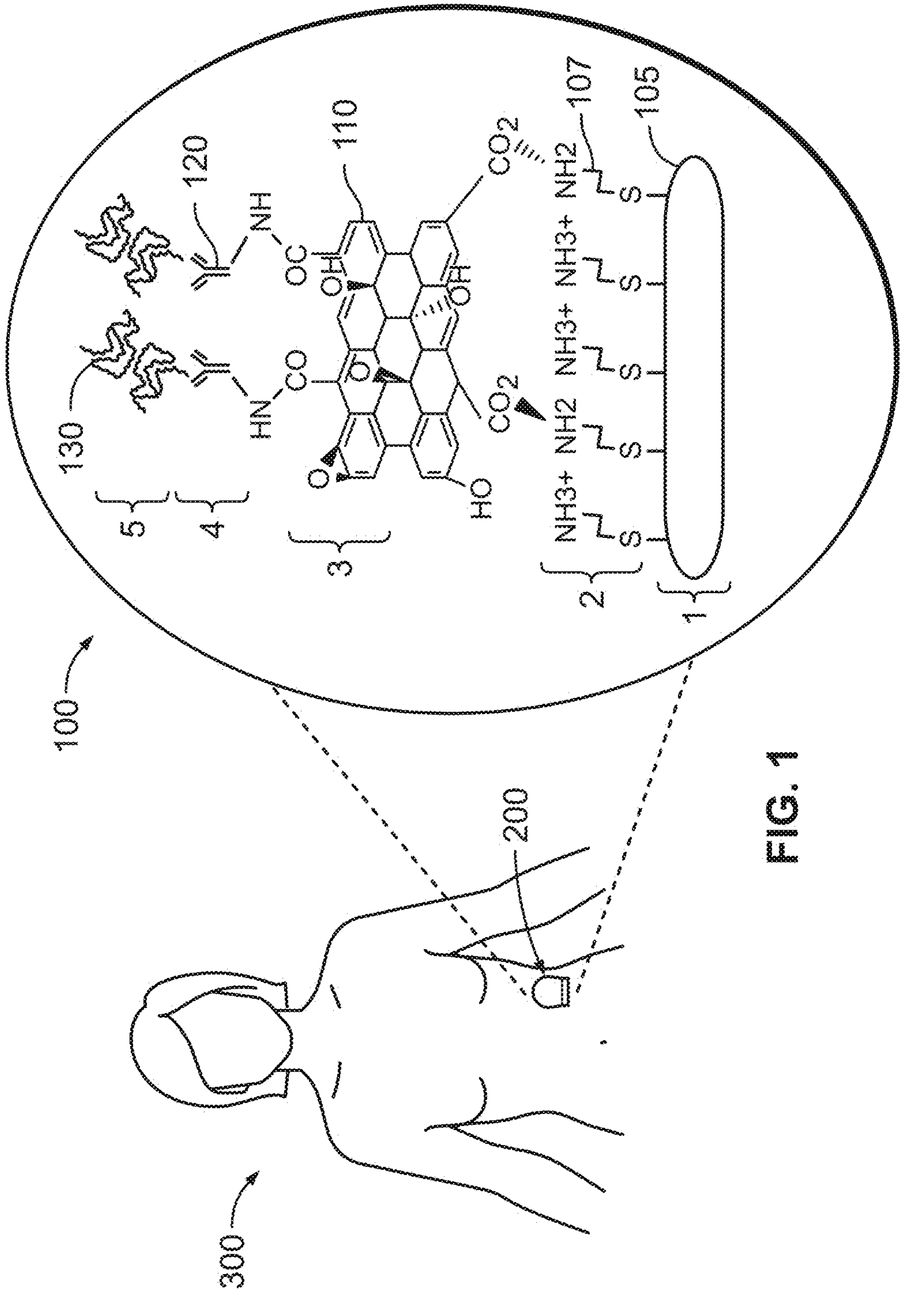
FIG. 1 depicts a layered receptor with at least one layer comprising graphene oxide and a biomarker binding layer configured to bind with a targeted biomarker.

In the present application the term "about" or "about the same" is construed as being at least 90% similar to the compared item. For example, an antibodies or proteins that are about the same as another antibody or protein would have at least 90% similarity to each other.

In the present application the term "essentially" or "essentially the same" or "substantially" is construed as being at least 95% similar to the compared item. For example, an antibodies or proteins that are about the same as another antibody or protein would have at least 95% similarity to each other.

In the present application antibody or protein "similarity" or "percent similarity" or "percent similar" refers to how similar two antibody proteins are when their amino acid sequences are compared. For purposes of the present application one amino acid is similar to another when substitution does not alter the folding structure or function of a protein to a great degree. These are often termed conservative substitutions. An amino acid residue, being one amino acid in a protein chain, is similar if it is identical to another amino acid residue in another protein chain. An amino acid residue in a protein chain is also similar if the amino acid is different but the differences do not affect folding and/or function of the protein chain.

Similarity can be compared using tools known in the art. The order of amino acids in a protein or the protein sequence is thought to hold the key for protein folding, i.e., each protein sequence folds into a unique shape to perform its function(s). While this relationship between sequence and structure holds true in most cases, some folded proteins may adopt multiple conformations corresponding to different functional states and a few protein sequences can fold into entirely different shapes (e.g., prion proteins). Sequence comparison is the most commonly used strategy for identifying homology, or similarity, between proteins and/or protein fragments or domains. The RCSB protein database website offers a sequence similarity search which allows either querying a protein data bank (PDB) to find similar proteins or comparing two or more input sequences. Although the most common method for sequence similarity searches is Basic Local Alignment Search Tool (BLAST, Altschul et al., Journal of Molecular Biology, Vol. 215, Issue 3, 5 Oct. 1990) the Sequence Similarity Search option available from RCSB.org uses the MMseqs2 software (Steinegger and Söding, Nature Biotechnology, Vol. 35, pp. 1026-1028, 16 Oct. 2017) to find similar protein and nucleic acid sequences. The MMseqs2 tool is similar to BLAST but achieves better performance at comparable levels of sensitivity. The search is dependent on a user-defined "sequence identity cutoff". During the search, each structure in the archive is aligned with the target structure, and the number of identical amino acids is tallied. A BLAST comparison, BLASTN, can be performed on the National Institute of Health (NIH) government website. Any of these tools may be used to assess or define similarity of antibodies, proteins, protein or antibody fragments or portions, including binding regions.

In the present application the term "amino acid" or "amino acid residue" refers to a molecule that contains both amino ($NH_3^+$) and carboxyl groups ($COO^-$). Amino acids may be l- or d-stereoisomers and are the building blocks of protein molecules. While most amino acids have the basic formula RCHNH2COOH, amino acids with other substitutions are possible. For purposes of the present application, an "amino acid" refers to any molecule that can be bound to another amino acid to form a peptide chain. Common substitutions in amino acid molecules include but are not limited to N- and/or C-terminus capping and side chain modification. Other non-standard amino acids may include β-amino acids and γ-amino acids. Any stereoisomer, substituted amino acid molecule, capped amino acid molecule, modified amino acid molecule, β, γ, or any other modification of an amino acid will fall within the definition of an amino acid for purposes of the present application.

Figure 2:
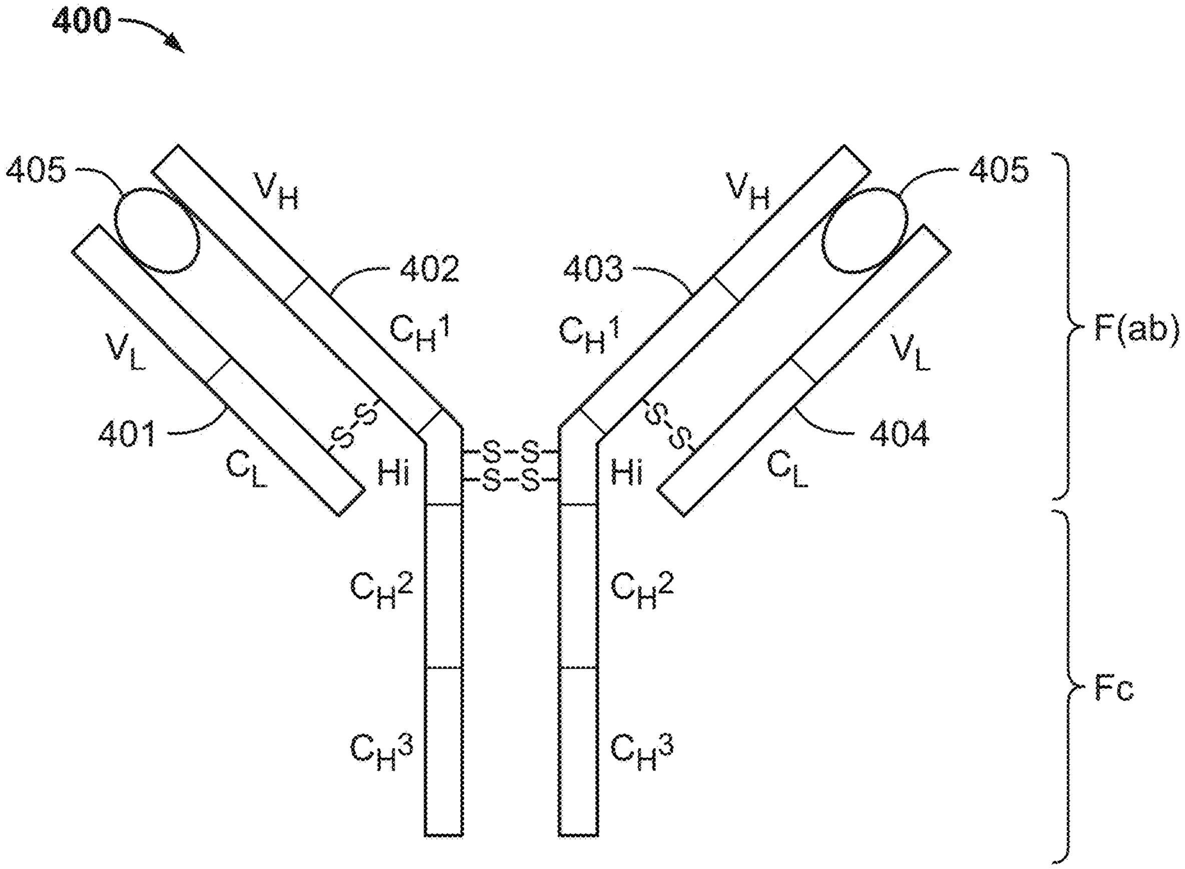
FIG. 2 illustrates part of an antibody.

In the present application the term "antibody" refers to a protein molecule that can bind a biomarker. An "antibody" FIG. 2, 400 may include whole naturally occurring antibodies, fragments of naturally occurring antibodies, chimeric antibodies, humanized antibodies, mutated antibodies, and non-naturally occurring antibodies. Antibodies in nature exist as one or more copies of a Y-shaped unit composed of four polypeptide chains 401, 402, 403, 404 as depicted in FIG. 2. Each Y unit contains two identical copies of a heavy chain (H) 402, 403 and two identical copies of a light chain (L) 401, 404. Heavy and light chains differ in their sequence and length and are bound together by sulfide bonds. The top of the Y shape contains the variable region (V), also known as the fragment antigen-binding (F(ab)) region. These F(ab) regions form the antigen binding sites 405 because they bind tightly to a specific part of an antigen or biomarker. The Y-shape of an antibody can be cleaved into three fragments by the proteolytic enzyme pepsin: two F(ab) regions and an Fc region. The F(ab) regions contain the variable domain that binds to cognate or bind to specific antigens or biomarkers. The antibody base consists of constant domains (C) and forms the fragment crystallizable region (Fc). The Y-shaped antibody is joined in the middle by a flexible hinge region (Hi). Antigen binding occurs at the variable domain (V), consisting of immunoglobulin heavy (H) and light chains (L). including: $V_H$—heavy chain variable domain; $V_L$—light chain variable domain; $C_H$—heavy chain constant domain; and $C_L$—light chain constant domain. An antibody may be classified by the heavy chain constant domain or region in types including IgG, IgM, IgA, IgD, and IgE. As such an antibody or antibody fragment for binding a biomarker, as defined herein, may comprise the variable domains of an antibody.

In the present application a "binding region" or "binding region of the antibody" is a region, span, or group of amino acids of an antibody that bind an epitope.

In the present application an "epitope" is a binding agent, region of a molecule, or group, or span of amino acids, that specifically binds to a binding region of an antibody. Example epitopes are listed in Table. 2.

In the present application a "biomarker" is any molecule or compound found in a patient that can bind selectively to an antibody.

In the present application a "patient" is any living form including a human or animal.

In the present application a "protein" or "peptide" is a molecule comprised of a chain of amino acids linked or bonded together. Therefore, a protein or peptide may be a complete naturally occurring protein or a fragment or domain of a naturally occurring protein, or a synthetic or partially synthetic protein.

In the present a "printed circuit board" or "PCB", also known as a printed wiring board (PWB), refers to a specific medium used to connect wire components to one another. A PCB is formed like a laminated sandwich of repeating conductive and insulating layers, wherein the conductive layers are designed with traces, planes, and other features which may be laid or etched on one or more sheet layers and/or laminated onto and/or between the layers of nonconductive substrates. PCBs can be used to connect or "wire" components to one another in an electronic circuit. Electrical components may be fixed to a conductive pad on the outer layers generally via soldering which electrically and physically connects the components to the board. Other manufacturing processes add vias, or metal-lined drilled holes, which enable electrical interconnections between conductive layers, to boards with more than one single side.

In the present application a "processor" or "central processing unit" or "CPU" refers to a hardware component that carrier out instruction from a program such as a software program. A CPU may receive instructions from a memory or program, optionally decode them, and perform the instructions, as well as control data flow. In a CPU the arithmetic logic unit (ALU) may perform arithmetic and logical operations on data. A CPU may contain a register or small memory unit that temporarily holds data, instructions, and memory addresses.

In the present application a "memory" or "memory unit" is a hardware component that stores data and instructions including programs such as software programs. A memory unit may comprise random access memory (RAM) and read-only memory (ROM).

In the present application a device that is "connected", such as a biosensor that is connected to an application, processor, memory unit, handheld or other computing device and/or display device, is connected such that data may flow between the two devices either via wireless or wired connection.

In the present application a "wireless" connection between two devices may be achieved with or without routers, access points, and adapters via Wi-Fi, cellular networks, Bluetooth, and/or satellite networks, or other technology.

In the present application, a "computer program" or "program" or "software program" or "application" or "software application" or "app" is a set of instructions that tell a computer how to perform a task.

In the present application a "display" is a device with a screen that shows rendered electronic images. For example, data from a biosensor of the present application may be displayed on a display or screen of a device connected to the biosensor.

In the present application "self-assembly" is a process where components, being molecules, particles, polymers, antibodies, minerals, compounds, chemicals, or the like, spontaneously form an ordered structure without external direction. Self-assembly can occur at molecular or macroscopic levels. Self-assembly may occur through local interactions between components, such as hydrogen bonds, van der Waals forces, and electrostatic interactions. These interactions can be attractive or repulsive, depending on the electrical charges and magnetic properties of the components.

Description

The present disclosure pertains to an apparatus and method for detecting biomarkers comprising of a layered receptor 100, as depicted in FIG. 1. The method may comprise a method for diagnosis and monitoring disease or other health indicator. FIG. 1 depicts the layered receptor 100 with at least one layer comprising graphene oxide 110 and a biomarker binding layer 120 configured to bind with a targeted biomarker 130. The layered receptor 100 depicted by FIG. 1 includes, in sequence, at least one first layer comprising a polymer and metal nanoparticles layer 105, at least one second layer comprising an organosulfur layer 107, at least one third layer comprising a graphene oxide layer 110, and at least one fourth layer comprising a biomarker binding layer 120. The illustrated layered receptor 100 is depicted with biomarker 130, which is found in a patient's 200 body or bodily fluid, and which binds to, in the present disclosure's example, an antibody on the biomarker binding layer 120 specifically and selectively.

The polymer and metal nanoparticles, or metal nanoparticle polymer layer FIG. 1, 105 comprises a polymer, being a biocompatible polymer which facilitates a strong adhesion to the metal nanoparticle while maintaining electrochemical stability for impedance-based sensing. These polymers may include an amine-functionalized polymer including but not limited to amines including methylamines, or methanamines, being organic compounds represented by the base formula $CH_3NH_2$, which may include but are not limited to monemethylamine (MMA), dimethylamine (DMA), trimethylamine (TMA), and/or methylamine hydrochlorides, including but not limited to 1-pyrene-methylamine (PMA) with structure illustrated below as Structure 1. Alternate polymers for the polymer and metal nanoparticles layer 105 include in non-limiting examples acrylic polymers such as polymethylacrylate, polyfunctional adhesion polymers, surface-assisted polymers, biopolymeric coatings, as well as thiolated, catechol-based, polysaccharide-based, or conductive polymers.

STRUCTURE 1

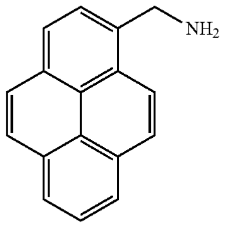

The polymer and metal nanoparticles, or metal nanoparticle polymer layer FIG. 1, 105 comprises inert metal nanoparticles, noble metal nanoparticles, or noble metal-based multimetallic nanoparticles (NMMNs) such as but not limited to nanoparticles of gold (Au), iridium (Ir) iron (Fe), platinum (Pt), palladium (Pd), Rhodium (Rh), Ruthenium (Ru), and silver (Ag), or mixtures thereof. Synthesis of metal nanoparticles is known in the art and may include but is not limited to co-reduction, thermal decomposition, solvothermal, incipient wetness impregnation, and/or seed-mediated synthesis methods. The polymer facilitates molecular stability and supplies binding opportunity of the metal nanoparticles which enable binding to a carbon nanotube. The polymer and metal nanoparticles layer 105 is formed via interaction between the polymer and metal nanoparticles via physical interactions such as van der Waals forces, hydrogen bonding, or π-π interactions and attached to at least one CNT FIG. 3, 505 via dip coating or other means as described herein.

The organosulfur layer FIG. 1, 107 comprises in one example an organosulfur, or aminothiol, such as cysteamine, represented by the formula $HSCH_2CH_2NH_2$. The organosulfur 107 layer is formed and attached, being coated onto the polymeric and metal nanoparticle layer 100 with methods described herein. Examples of organosulfurs appropriate for the organosulfur layer 107 include thiols, disulfides, thiol-functionalized polymers, thioethers, and dithiocarboxylates.

The graphene or graphene oxide (GO) layer FIG. 1, 110 comprises graphene oxide. Graphene is a carbon allotrope consisting of a single layer of carbon atoms arranged in a honeycomb planar nanostructure. GO is a nanomaterial made of carbon synthesized by the chemical oxidation of graphite or carbon nanofibers via methods known in the art via chemical or electrochemical oxidation with the resulting graphite oxide being exfoliated into GO. The GO layer 110 is formed via common techniques known in the art, for example a dip coating process. In one non-limiting example, the CNT is immersed in a PMA and metal nanoparticle solution to coat the CNT with a PMA metal nanoparticle layer in a first step. Following the first step, the CNT-PMA-metal nanoparticle substrate is dipped in an organosulfur layer in a second step, in the third step the GO layer is added. Other methods of coating known in the art may be employed such as but not limited to drop casting, wherein a precise volume is dropped onto a substrate and allowed to dry under controlled conditions, spin coating, wherein a small amount of solution is placed on the substrate and then spun at high speeds to create a thin, uniform layer, electrodeposition, or electrochemical deposition wherein the substrate is immersed in a solution and electric potential is applied causing the material to deposit onto the electrode, spray coating, wherein the solution is atomized into fine droplets and sprayed onto the substrate, and the Langmuir-Blodgett (LB) Technique wherein a monolayer of material is spread on a water surface then transferred to the substrate via vertical dipping.

Multiple bonding events or interactions may play a role in forming the layered receptor 100. For example, the GO may bind to the PMA layer via carboxyl (COOH) groups, the GO may react with amine groups ($NH_2$) to form amide bonds through coupling. The graphene oxide FIG. 1, 110 layer provides structural support and enhances the stability of the receptor, while the biomarker binding layer 120 is specifically designed to bind with a targeted biomarker. This targeted binding is for the detection of specific biomolecules or biomarkers in a sample or biofluid of a patient 300. The organosulfur-functionalized graphene oxide layer provides high-affinity binding to biomarkers.

The biomarker binding layer FIG. 1, 120 may comprise a biomarker binding layer agent such as at least one type of antibody or antibody fragment. Antibodies in nature exist as one or more copies of a Y-shaped unit composed of four polypeptide chains 401, 402, 403, 404 as depicted in FIG. 2. Each Y unit contains two identical copies of a heavy chain (H) 402, 403 and two identical copies of a light chain (L) 401, 404. Heavy and light chains differ in their sequence and length and are bound together by sulfide bonds. The top of the Y shape contains the variable region (V), also known as the fragment antigen-binding (F(ab)) region. These F(ab) regions form the antigen binding sites 405 because they bind tightly to a specific part of an antigen or biomarker. The Y-shape of an antibody can be cleaved into three fragments by the proteolytic enzyme pepsin: two F(ab) regions and an Fc region. The F(ab) regions contain the variable domain that binds to cognate or bind to specific antigens or biomarkers. The antibody base consists of constant domains (C) and forms the fragment crystallizable region (Fc). The Y-shaped antibody is joined in the middle by a flexible hinge region (Hi). Antigen binding occurs at the variable domain (V), consisting of immunoglobulin heavy (H) and light chains (L). including: $V_H$—heavy chain variable domain; $V_L$—light chain variable domain; $C_H$—heavy chain constant domain; and $C_L$—light chain constant domain.

As such, complete antibodies, natural or engineered, may be employed in the biomarker binding layer FIG. 1, 120. In alternate embodiments antibody fragments, or engineered antibody fragments, including antibody regions, for example Fab regions, $V_H$ and $V_L$ domains, or complementary determining regions (CDRs), may be employed and linked to the graphene oxide layer 110 instead of whole antibodies. Antibodies, or antibody fragments derived from antibodies, whether natural or engineered, and their target biomarkers as well disease application, which may be useful for the disclosed apparatus and method include but are not limited to those listed in Table 1 below.

TABLE 1

| Antibody | Biomarker | Disease Application |
|---|---|---|
| 6E10 | Amyloid-beta (Aβ) peptides | Alzheimer's Disease (AD) |
| 4G8 | Amyloid-beta (Aβ) peptides | Alzheimer's Disease (AD) |
| AT8 | phosphorylated and total Tau proteins | Alzheimer's Disease (AD) |
| HT7 | phosphorylated and total Tau proteins | Alzheimer's Disease (AD) |
| SMI31 | Neurofilament light chain (NfL) | Multiple Sclerosis (MS) |
| SMI32 | Neurofilament light chain (NfL) | Multiple Sclerosis (MS) |
| Anti-MBP antibody | Myelin Basic Protein (MBP) | Multiple Sclerosis (MS) |
| Anti-SOD1 (targets mutated and wild-type SOD1) | Superoxide Dismutase 1 (SOD1) | Amyotrophic Lateral Sclerosis (ALS) |
| Anti-TDP-43 (targets phosphorylated and total TDP-43) | TAR DNA-binding protein 43 (TDP-43) | Amyotrophic Lateral Sclerosis (ALS) |
| MW1 | Huntingtin protein (mHTT) | Huntington's Disease (HD) |
| 3B5H10 (targets mutant huntingtin fragments) | Huntingtin protein (mHTT) | Huntington's Disease (HD) |
| αSyn-211 | alpha-synuclein | Parkinson's Disease and Lewy Body Dementia |

TABLE 1-continued

| Antibody | Biomarker | Disease Application |
|---|---|---|
| LB509 | alpha-synuclein | Parkinson's Disease and Lewy Body Dementia |
| 5G4 | alpha-synuclein | Parkinson's Disease and Lewy Body Dementia |
| Anti-TDP-43 | TDP-43 | Frontotemporal Dementia (FTD) |
| AT8 | Tau proteins | Frontotemporal Dementia (FTD) |
| HT7 | Tau proteins | Frontotemporal Dementia (FTD) |
| Tau-5 | Tau proteins | Frontotemporal Dementia (FTD) |

As described above, certain regions of a biomarker binding molecule bind a biomarker. As such regions of antibodies identified as binding regions of different biomarkers are listed in Table 2. Each antibody the binding site sequence, or epitope, is located in, the biomarker, disease application, and binding site sequence is presented.

TABLE 2

| Antibody | Biomarker | Disease Application | Binding Site Sequence (Epitope) | Reference |
|---|---|---|---|---|
| 6E10 | Amyloid-beta (Aβ) peptides | Alzheimer's Disease (AD) | Residues 4-10 of Aβ: FRHDSGY | Source 1 |
| 4G8 | Amyloid-beta (Aβ) peptides | Alzheimer's Disease (AD) | Residues 18-23 of Aβ: LVFFAED | Source 2 |
| AT8 | Phosphorylated Tau proteins | Alzheimer's Disease (AD), Frontotemporal Dementia (FTD) | SGYSSPG(pS)PG(pT)PG(pS)RSR | Source 3 |
| HT7 | Total Tau proteins | Alzheimer's Disease (AD), Frontotemporal Dementia (FTD) | Binds to residues 159-163 of Tau: PPGQK | Source 4 |
| αSyn-211 | Alpha-synuclein | Parkinson's Disease, Lewy Body Dementia | Recognizes residues 121-125 of alpha-synuclein: DNEAY (SEQ ID. NO. 5) | Source 5 |

The biomarker binding layer 120 is prepared in solution for example via homogenous mixture and attached to the GO layer via a dip or other coating methods as described herein. The biomarker binding layer of the present disclosure was created using an anti-alpha-synuclein antibody similar to Syn-211 whose heavy and light chains, as well as heavy chain variable region and light chain variable region sequences are disclosed in Table 3 below.

Antibodies or antibody fragments that may be employed in the biomarker binding layer 120 to bind alpha-synuclein, i.e. those binding alpha-synuclein, may comprise binding regions, being binding site sequences, regions or portions of a larger protein that bind the epitope, such as a variable chain heavy region or the variable chain light region, which may be at least 90% similar to one of SEQ. ID. NOs. 1 and/or 3, or in other terms binding regions that are at least ninety percent of the amino acids are similar to SEQ ID NOs. 1 and/or 3 in Table 3, or at least 91% similar, or at least 92% similar, or at least 93% similar, or at least 94% similar, or at least 95% similar, or at least 96% similar, or at least 97% similar, or at least 98% similar, or at least 99% similar, or 100% similar to binding site sequences listed in Table 3.

Antibodies or antibody fragments used in the biomarker binding layer 120 to bind alpha-synuclein, i.e. those binding alpha-synuclein, may comprise binding regions, or site sequences that are at least 70% similar to SEQ. ID. NOs. 2 and/or 4, or in other terms at least seventy percent of the amino acids in the binding regions are similar to SEQ ID NOs. 2 and/or 4 in Table 3, or at least 71% similar, or at least 72% similar, or at least 73% similar, or at least 74% similar, or at least 75% similar, or at least 76% similar, or at least 77% similar, or at least 78% similar, or at least 79% similar, or at least 80% similar, or at least 81% similar, or at least 82% similar, or at least 83% similar, or at least 84% similar, or at least 85% similar, or at least 86% similar, or at least 87% similar, or at least 88% similar, or at least 89% similar, or least 90% similar, or at least 91% similar, or at least 92% similar, or at least 93% similar, or at least 94% similar, or at least 95% similar, or at least 96% similar, or at least 97% similar, or at least 98% similar, or at least 99% similar, or 100% similar to binding site sequences listed in Table 3.

Antibodies or antibody fragments used in the biomarker binding layer 120 to bind alpha-synuclein, i.e. those binding alpha-synuclein, may comprise sequences that are at least 60% similar to one or more of SEQ. ID. NOs. 1, 2, 3 and/or 4, or in other terms at least fifty percent of the amino acids are similar to SEQ ID NOs. 1, 2, 3, and/or 4 named in Table 3, or at least 61% similar, or at least 62% similar, or at least 63% similar, or at least 64% similar, or at least 65% similar, or at least 66% similar, or at least 67% similar, or at least 68% similar, or at least 69% similar, or at least 70% similar, or at least 71% similar, or at least 72% similar, or at least 73% similar, or at least 74% similar, or at least 75% similar, or at least 76% similar, or at least 77% similar, or at least 78% similar, or at least 79% similar, or at least 80% similar, or at least 81% similar, or at least 82% similar, or at least 83% similar, or at least 84% similar, or at least 85% similar, or at least 86% similar, or at least 87% similar, or at least 88% similar, or at least 89% similar, or least 90% similar, or at least 91% similar, or at least 92% similar, or at least 93% similar, or at least 94% similar, or at least 95% similar, or at least 96% similar, or at least 97% similar, or at least 98% similar, or at least 99% similar, or 100% similar to sequences listed in Table 3.

TABLE 3

| αSyn211 binding region | Sequence | SEQ ID. NO. |
|---|---|---|
| Heavy Chain Variable Region | XVQLLESGGGLVQPGGSLRLSCAASGFTFSSYAMSWVRQAPGKG<br>LEWVSAISGSGGDTYYADSVXGRFTISRDNSKNTLYLQMNSLRAE<br>DTAVYYCARGYGMDVWGQGTTVTVSS | 1 |
| Heavy Chain | XVQLLESGGGLVQPGGSLRLSCAASGFTFSSYAM<br>SWVRQAPGKGLEWVSAISGS GGDTYY<br>ADSVXGRFTISRDNSKNTLYLQMNSLRAEDTAVYYC<br>ARGYGMDVWG<br>QGTTVTVSSASTKGPSVFPLAPCSRSTSESTAAL<br>GCLVKDYFPEPVTVSWNSGALT SGVHTFP<br>AVLQSSGLYSLSSVVTVPSSSLGTKTYTCNVDHKPS<br>NTKVDKRVESKY GPPCPPCPA<br>PEAAGGPSVFLFPPKPKDTLMISRTPE<br>VTCVVVDVSQEDPEVQFNW<br>YVDGVEVHNAKTKPREEQFN<br>STYRVVSVLTVLHQDWLNGKEYKCKVSNKGLPS<br>SIEKTISKAKGQPREPQVYTLPPSQEEMTKNQVSLT<br>CLVKGFYPSDIAVEWESNGQ PEN<br>NYKTTPPVLDSDGSFFLY<br>SRLTVDKSRWEGNVFSCSVMHEALHNHYTQKS<br>LSLSLX | 2 |
| Ligh Chain Variable Region | DVVMTQSPLSLPVTLGQPASISCRSSQXLVHSDGNTYLMWFQQR<br>PGQSPRRLIYKVSXRNSGVPDRFSGSGSGTDFTLKISRVEAEDVGV<br>YYCMQGTKQYPTFGQGTK LEIK | 3 |
| Light Chain | DVVMTQSPLSLPVTLGQPASIS<br>CRSSQXLVHSDGNTYLMWFQQRPGQSPRRLIY<br>KVSXRNSGVPDRFSGSGSGTDFTLKISRVEAE<br>DVGVYYCMQGTKQYPTFGQGTK<br>LEIKRTVAAPSVFIFPPSDEQLKSGTASVVCLLNNFY<br>PREAKVQWKVDNALQSGN SQESVTEQDSKDS<br>TYSLS STLTLSKADYEKHKVYACE<br>VTHQGLSSPVTKSFNRGE C | 4 |

Figure 3:
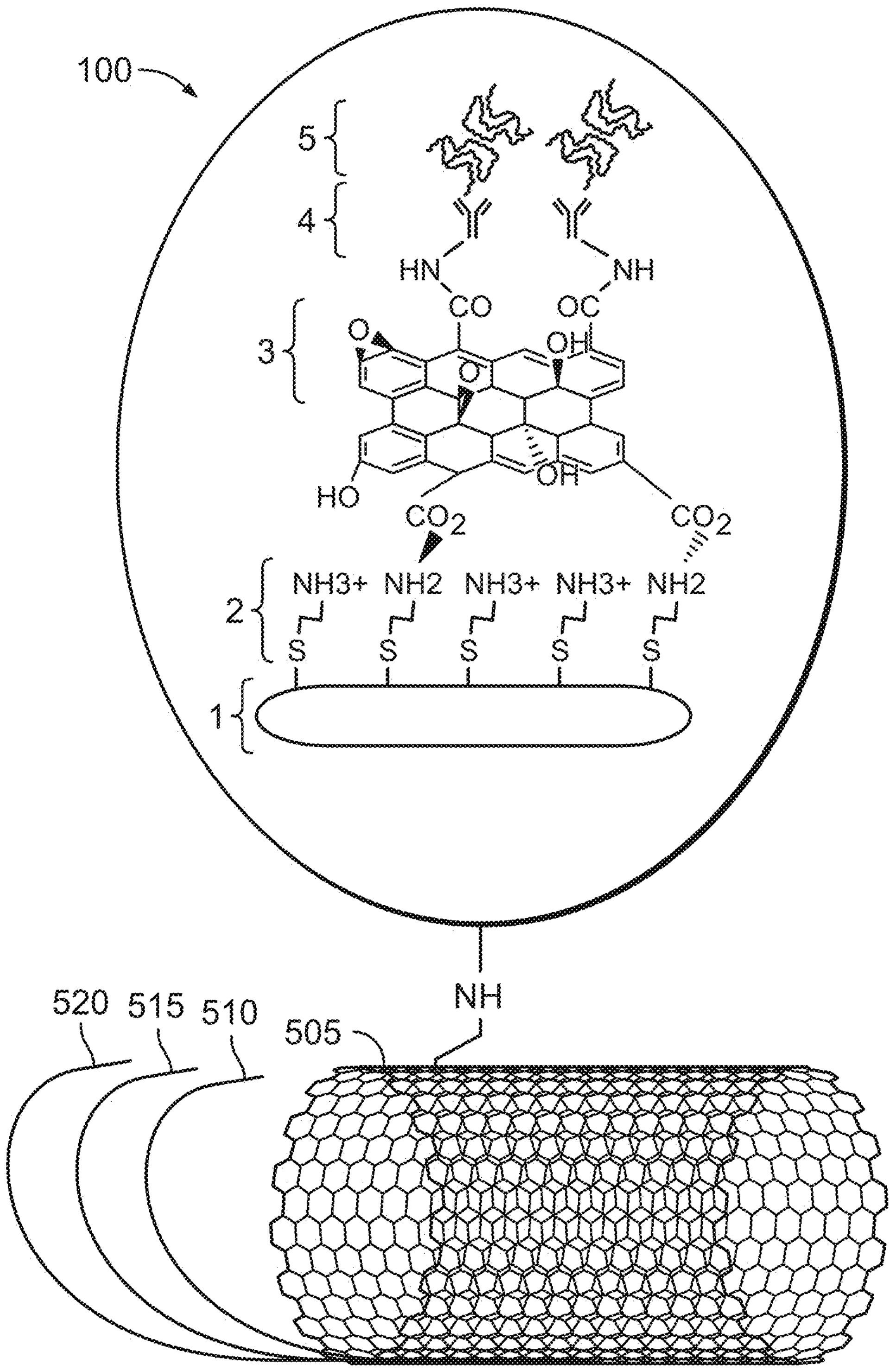
FIG. 3 depicts the layered receptor shown by FIG. 1, with the addition of an electrode layer comprising Carbon Nanotubes (CNT) and other electrodes.

FIG. 3 depicts the layered receptor 100 illustrated in FIG. 1 attached to an electrode layer comprising Carbon Nanotubes (CNT) 505. To attach CNT to the layered receptor 100, the CNT are washed to remove impurities and a dip coating or other coating process is employed as described herein]. Other example electrode in non-limiting examples may include consumable and non-consumable electrodes, bare electrodes, low-hydrogen electrodes, aluminum MIG electrodes, light coated electrodes, alternating current arc welding electrodes, metal-cored wire electrodes, metal electrodes such as silver or other metal wire electrodes. Biocompatibility of all materials may be considered when choosing appropriate materials.

In one example, the CNT with layered receptor 100 serves as a working electrode, measuring impedance when biomarker-binding events occur altering impedance. A reference electrode (RE) completes the circuit, applying for instance an AC voltage signal and measuring impedance simultaneously. In another example a counter electrode (CE) is also employed. In this three-wire or three-electrode configuration, the CNT electrode serves as the WE, the RE provides a stable potential, and the CE balances the applied current. In another example, a voltage sensing electrode (SE) is employed. In this four-electrode or four-wire configuration, the CNT serves as the WE, the RE maintains a stable potential, the CE allows current to flow, and the SE placed near the WE, for example, measures voltage drop independently without drawing current. Other embodiments of the device may employ more than four wires or electrodes in a multi-electrode configuration wherein multiple SEs are positioned at multiple points to further improve impedance resolution and spatial accuracy. In these multi-electrode configurations, the CNT forms the WE, the RE provides stability, the CE completes the circuit, and multiple SEs measure impedance at different locations. The RE, CE, and SEs may be formed from the same or different materials.

The biosensor FIG. 1, 200 may further employ a working electrode comprising Carbon Nanotubes (CNT) 505 as shown in FIG. 3 and a reference electrode 510, and/or other additional electrodes 515, 520 connected to the layered receptor. The working electrode may be attached to a sampling apparatus 220, which may be a sampling electrode, being a conductive needle or wire for implantation into a patient 300. The sampling apparatus, being in one embodiment a conductive needle or wire can be made from fully conductive materials, in non-limiting examples platinum, gold, silver, stainless steel, or titanium, or a hybrid design, such as plastic or polymer tubing with an embedded conductive core, in non-limiting examples gold, silver, or CNT-based materials).

The biosensor patch 200 may detect events that involve the targeted biomarker FIG. 1, 130 binding with the biomarker binding layer 120. Biomarkers 130 that may be bound to the biomarker binding layer 120 include proteins, peptides, or other biomolecules found in a patient 300. These may comprise monomers, dimers, or oligomers of proteins or peptides, or for example abnormally aggregated proteins. This detection is achieved by measuring changes in impedance to multiple frequencies of an alternating current voltage signal applied through a patient's body fluid between the working electrode and the reference electrode. The patient's 300 body fluid may comprise in non-limiting examples blood, plasma, sweat, serum, cerebral spinal fluid, saliva, urine, tears or nasal discharge. Patients may include but are not limited to human or animal patients.

Figure 4:
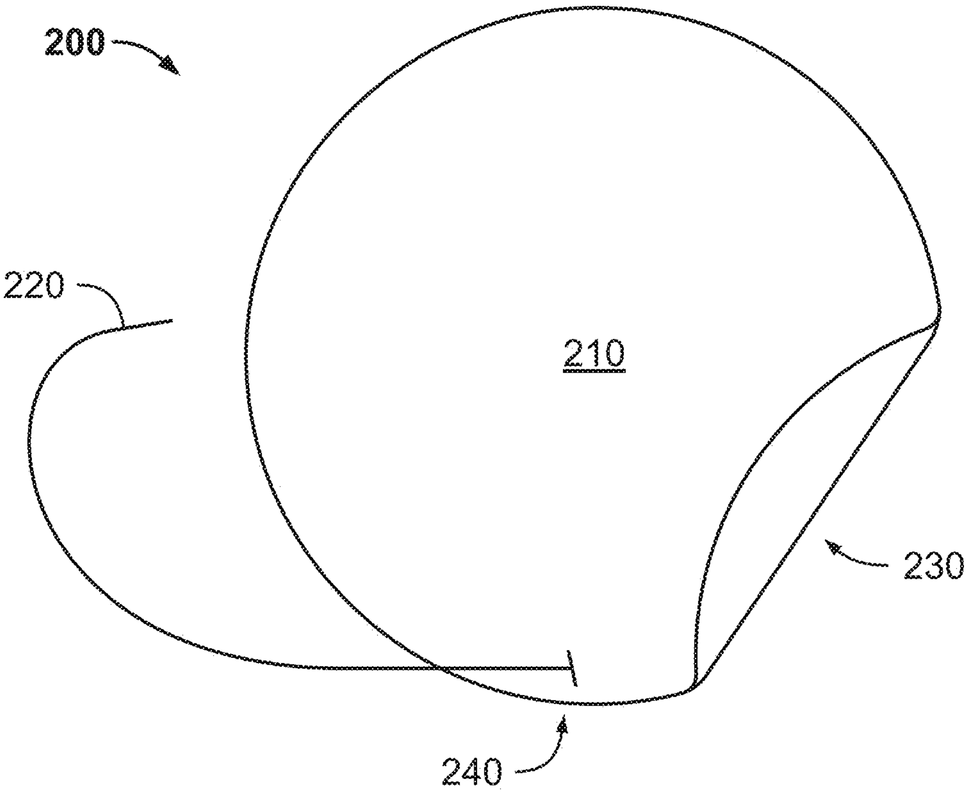
FIG. 4 illustrates a biosensor patch of the present disclosure.

As illustrated in FIG. 4, a wearable biosensor patch 200 may provide a minimally invasive wearable device equipped with the custom-designed biochemical, or layered receptor 100 created for continuous, direct quantification of biomarker levels in patients. The biosensor patch 200 uses advanced materials and electrochemical impedance spectroscopy (EIS) to monitor biomarkers crucial for understanding disease progression. One implementation of biosensor patch 200 use may provide real-time monitoring of biomarkers in a patient 300. The biosensor patch 200 may be configured to use EIS to enhance efficacy by providing high sensitivity and precise quantification of changes in biomarker levels. The biosensor patch 200 may connect to a system-on-a-chip or a specifically designed printed circuit board (PCB), housed in the biosensor patch 200, for impedance measurement.

A patient 300 may use the biosensor patch 200 by applying the adhesive area 230 or attachment component to their skin with an applicator or adhesive for optimal adherence and precise application in a specified area. The biosensor patch 200 may be worn continuously for real-time monitoring, and the rate of biomarker 130 aggregation or binding is measured by the EIS system and displayed in the monitoring app/device or connected systems.

The biosensor patch 200 comprises electronic and electromechanical hardware governed by software stored in the memory executing a computer-implemented process or program via a processor. The biosensor patch 200 includes a custom-designed biosensor patch 200 that may be configured to target various biomarkers 130 using techniques in accordance with the teaching of the present disclosure.

As described above, the biosensor patch 200 may comprise an exemplary electrode configuration including three electrodes: a working electrode 505 coated with the layered receptor layers 100 including antibodies, a reference electrode 510 configured to provide a stable reference potential, and a counter electrode 515 configured to complete the electrical circuit. In an illustrative example shown in FIG. 3, the working electrode may be a CNT with the layered receptor built on the electrode surface which will be attached to a sampling apparatus 220, being a conductive needle or wire, wherein the sampling apparatus 220 contacts a biofluid of the patient 300.

The biosensor patch 200 may comprise a power source or battery. The power source or battery may comprise a rechargeable battery. Other example batteries include but are not limited to thin-film batteries, which are lightweight and flexible for integration into the patch; supercapacitors, which can provide quick bursts of power and recharge efficiently; energy harvesting technologies such as thermoelectric generators, using body heat, or photovoltaic cells, that employ ambient light harvesting, which could extend battery life without requiring user movement; and wireless power transfer, such as inductive or RF, or radio-frequency charging, enabling continuous power delivery without direct electrical connections.

The biosensor patch 200 comprises a flexible housing 210 to contain and protect the layered receptor 100 and receptor layers 105, 107, 110, 120, electrodes 505, 510, 515, 520 electronics and processing components. The flexible housing 210 may be a plastic, rubber, or fabric, woven, or non-woven whether natural or synthetic, hydrogel or hydrocolloid materials, or combinations thereof, being compatible and safe to be used with or on patient 300 tissue. The flexible housing 210 may be of any appropriate shape or size to house the components of the biosensor patch 200.

The biosensor patch 200 and/or flexible or non-flexible housing 210 of the biosensor patch 200 may comprise an attachment component 230 for attaching to a patient's tissue or body. Attachment component 230 in non-limiting examples may be clamps, clips, prongs, adhesives or glues safe for contact with patient tissue or skin. Examples of adhesives that may be safe for attachment to patient tissue or skin include acrylic, silicone, cyanoacrylate, and medical-grade adhesives. Non-limiting examples of these include pressure-sensitive silicone, 2-Octyl-cyanoacrylate, n-2-Butyl-cyanoacrylate, 2-Ethyl-cyanoacrylate, and polyisobutylenes (PIBs). The adhesive may be semi-permanent. In other embodiments the biosensor may be housed in a non-flexible material.

Further the biosensor patch 200 may comprise an exterior sampling apparatus 220 to contact the bodily fluid of the patient 300. This sampling apparatus may protrude for instance from an opening 240 in the biosensor patch. The sampling apparatus may be or form a sampling electrode as described above, wherein the sampling apparatus/sampling electrode is the working electrode.

The flexible housing 210 itself may be constructed of at least one piece or at least two pieces that encapsulate the working components, the layered receptor, electrodes, processor, memory, and other components. The flexible housing 210 material may be sealed or closed permanently such as with a permanent adhesive. In an alternate embodiment, the flexible housing may be sealed in semi-permanent, or non-permanent manner to allow for maintenance of the inner working components.

The attachment component 230 may enable the patient 300 to wear the biosensor patch 200 for elongated periods of time which may include at less than thirty seconds, or as long as 1 minute, or half an hour, or 1 hour, or 2 hours, or 3 hours, or 4 hours, or 5 hours, or 6 hours, or 7 hours, or 8 hours, or 9 hours, or 10 hours, or 11 hours, or 12 hours, or 13 hours, or 14 hours, or 15 hours, or 16 hours, or 17 hours, or 18 hours, or 19 hours, or 20 hours, or 21 hours, or 22 hours, or 23 hours, or 24 hours, or 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or 21 days, or 22 days, or 23 days, or 24 days, or 25 days, or 26 days, or 27 days, or 28 days, or 29 days, or 30 days, or 31, days, or one week, or two weeks, or three weeks, or four weeks, or five weeks, or six weeks, or 7 weeks, or 8 weeks, or more. Wearing the biosensor patch 200 for elongated periods of time allows for real-time monitoring over a designated period of time to store data with a time and date component to track trends in biomarker levels over time. This allows creation of personalized treatment plans, understanding of disease progression, thereby improving patient care and disease understanding.

The steps performed by the biosensor patch 200 to obtain a measurement of biomarker 130 levels include application of voltage, interaction with biomarkers, impedance measurement, data analysis, and reporting. The processed information may then be prepared for transmission to an external system for further analysis or review.

The biosensor patch 200 platform software may be configured to perform data acquisition and processing comprising periodically measuring the biosensor's response using EIS, converting analog signals to digital using an Analogto-Digital Converter (ADC), and processing the data to extract impedance information related to the biomarker 130.

An exemplary algorithm for EIS-based biomarker measurement using a microcontroller-based wearable biosensor patch 200 may comprise initializing the microcontroller, configuring the biosensor electrodes, setting up communication for data transmission, defining constants and parameters, initializing the ADC for analog signal conversion, reading impedance response from the biosensor, converting impedance to biomarker concentration using calibration factors, displaying biomarker concentration on the wearable device screen, checking for abnormal readings, transmitting data to a smartphone app or cloud server, and "sleeping" for a predefined interval. A "sleeping" mode may refer to a low-power mode wherein the microcontroller reduces energy consumption between measurements. The system can wake up at set intervals or dynamically based on biomarker fluctuations. For example, if a sudden change in biomarker concentration is detected, it could trigger an immediate reading rather than waiting for the next scheduled measurement.

Impedance measurements can be carried out at various frequencies of the alternating current voltage signal to obtain a comprehensive understanding of the biomarker-antibody binding kinetics. By analyzing the impedance response at different frequencies, additional information about the interaction dynamics and binding strength can be obtained, allowing for a more detailed characterization of the biomarker detection process. Frequencies may range from for examples 0.5 Hz to 100 kHz. For example the frequence used may be at least 10 Hz, or at least 11 Hz, or at least 12 Hz, or at least 13 Hz, or at least 14 Hz, or at least 15 Hz, or at least 16 Hz, or at least 17 Hz, or at least 18 Hz, or at least 19 Hz, or at least 20 Hz, or at least 21 Hz, or at least 22 Hz, or at least 23 Hz, or at least 24 Hz, or at least 25 Hz, or at least 26 Hz, or at least 27 Hz, or at least 28 Hz, or at least 29 Hz, or at least 30 Hz, or at least 31 Hz, or at least 32 Hz, or at least 33 Hz, or at least 34 Hz, or at least 35 Hz, or at least 36 Hz, or at least 37 Hz, or at least 38 Hz, or at least 39 Hz, or at least 40 Hz, or at least 41 Hz, or at least 42 Hz, or at least 43 Hz, or at least 44 Hz, or at least 45 Hz, or at least 46 Hz, or at least 47 Hz, or at least 48 Hz, or at least 50 Hz, to 100 KHz, or more, in for instance 0.1 Hz, or 0.2 Hz, or 0.3 Hz, or 0.4 Hz, or 0.5 Hz, or 0.6 Hz, or 0.7 Hz, or 0.8 Hz, or 1 Hz increments, or larger increments for instance 2 Hz increments, or 3 Hz, or 4 Hz, or 5 Hz, or 10 Hz, or 20 Hz, or 30 Hz, or 40 Hz, or 50 Hz, 100 Hz, or more increments.

To detect events such as the binding of the targeted biomarker 130 with the biomarker binding layer 120, a working electrode made of carbon nanotubes (CNT) 505 is connected to the layered receptor 100. The CNT working electrode offers high electrical conductivity and a large surface area, which is beneficial for efficient electron transfer during the detection process. Additionally, a reference electrode 510 is connected to the layered receptor 100 to provide a stable reference point for measuring electrical signals.

The detection of binding events of a biomarker 130 to the biomarker binding layer 120 is achieved by measuring changes in impedance. Impedance measurements are taken at multiple frequencies of an alternating current voltage signal that is applied through a patient's body fluid. By analyzing the impedance changes at different frequencies, the system can gather detailed information about the interactions between the biomarkers and the receptor. This allows for precise and sensitive detection of specific biomolecules in the patient's sample or biofluid. For example, in a diagnostic application, this method could be used to detect the presence of a particular protein biomarker in a patient's blood sample.

EXAMPLES

Example 1

In an example, a CNT was dip coated by immersion in the polymer and metal nanoparticle layer. To form the polymer and metal nanoparticle layer, PMA solution was prepared in ethanol. A gold nanoparticle solution was prepared using $HAuCl_4$, cetyltrimethylammonium bromide (CTAB), and ascorbic acid, and CTAB and gold were mixed. Following the PMA solution was added while stirring and ascorbic acid added dropwise to reduce gold. The solution was stirred for 12 hours, then washed with water and ethanol and dried for 1 hour (hr). In order to functionalize the organosulfur layer, or cysteamine layer, cysteamine was dissolved in ethanol and the substrate, CNT-PMA-Au substrate, was immersed in the cysteamine ethanol solution overnight at 4° C., following which the substrate was washed with ethanol and allowed to dry for 1 hr. To add the GO layer, the substrate was immersed in graphene oxide solution overnight. Then the substrate was put in an EDC/NHS solution and incubated for 40 minutes (min) to activate bonding sites. An EDS/NHS solution uses 1-ethyl-3-(3-dimethylaminopropyl) carbodiimide (EDC) and N-hydroxysuccinimide (NHS) to link amine-containing molecules to carboxyl groups. The substrate was washed with ethanol and allowed to dry 1 hr. The αSyn antibody was prepared in a solution of phosphate buffered saline (PBS) solution, then the substrate was immersed overnight in the antibody-PBS solution at 4° C. Then, the substrate with antibody attached was washed in ethanolamine for 20 min, washed with water, let dry for 1 hr, and stored in a refrigerator at about 40° C. to form the layered receptor 100.

Example 2

Figure 5:
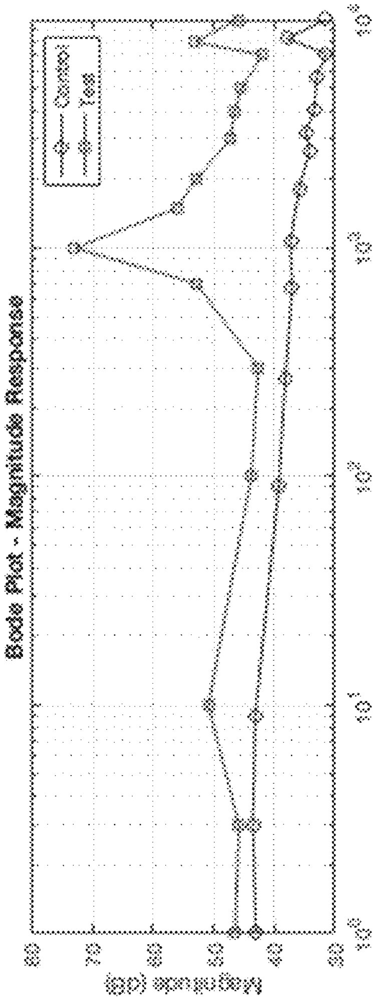
FIG. 5 illustrates impedance measured from bodily fluid upon binding events of the targeted biomarker to a biomarker binding layer.
Figure 6:
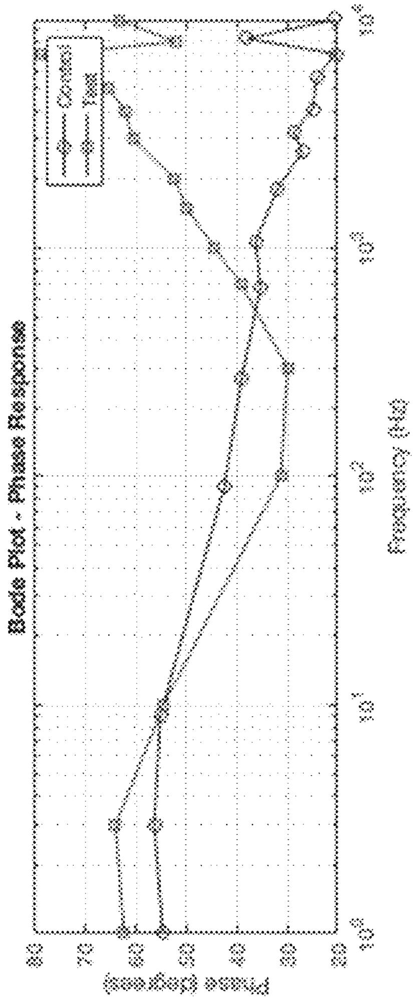
FIG. 6 illustrates a resistive response measuring a distinct separation between the control and test conditions across both magnitude and phase responses suggesting sensor detection of protein binding through impedance changes.

A layered receptor 100 was formed as described in Example 1. Sampling in blood occurred over a ten-minute timer period. The amount of recombinant alpha-synuclein protein was fixed in the solution at a controlled amount of 400 pM, about 5.8 pg/mL. FIGS. 5-6 illustrate data, in Bode plots, measured in a control and test fluid including the magnitude response of frequency (Hz) as in FIG. 5 and the phase response of frequency (Hz) correlating to binding events.

The Bode plot provides a detailed electrochemical fingerprint of the sensor's response to alpha-synuclein (αSyn) binding, revealing distinct impedance characteristics that validate the sensor's functionality. In the magnitude response, FIG. 5, the test condition exhibits a significant increase in impedance, particularly at mid-to-high frequencies, about 10 Hz to 10 kHz, compared to the control. This rise in impedance suggests that protein binding is creating a biological barrier on the sensor surface, restricting electron flow and altering the charge transfer resistance. At lower frequencies, about 1 Hz to 10 Hz, the impedance remains relatively stable, indicating that the surface is still partially open, allowing some charge accumulation. The phase response, FIG. 6 further confirms these molecular interactions by illustrating a clear transition from capacitive to resistive behavior. In the low-frequency range, the phase angle remains higher, about 80°, signifying capacitive charge storage, which suggests that the sensor surface is still able to accommodate electron displacement without significant obstruction. However, as frequency increases, the phase angle steadily decreases, approaching ~20° at high frequencies (~10 kHz), reflecting a resistive response. This shift indicates that the alpha-synuclein binding has significantly altered the electrochemical properties of the surface, impeding charge flow and increasing the overall resistance. The distinct separation between the control and test conditions across both magnitude and phase responses suggests that our sensor can reliably detect protein binding through impedance changes.

The impedance data show a clear relationship between alpha-synuclein concentration and the sensor's response. At 400 pM (about 5.8 pg/mL) of alpha-synuclein, the biosensor recorded a noticeable increase in impedance, especially between 1 kHz and 7 kHz. In this range, the test sample's impedance was about 100 ohms higher than the control (which had no biomarker). In this case, a 100-ohm shift corresponds to a concentration of 400 pM, showing that impedance changes can indicate how much biomarker is present.

Example 3

In an example, an exemplary biosensor patch 200 of the present disclosure will be designed to continuously monitor biomarker levels in bodily fluids, offering a non-invasive, real-time approach for detecting and tracking disease biomarkers and progression. The biosensor patch as described herein utilizes electrochemical impedance spectroscopy (EIS) integrated with the layers described above to detect binding of biomarkers to antibodies or antibody fragments contained thereon.

The biosensor patch may be calibrated, in one example, to detect the alpha-synuclein via capture with Syn-211, LB509, 5G4 antibodies, antibody fragments, binding regions and/or chimeric antibodies thereof utilized to produce a biosensor patch 200. As such the patch may be position on an end user or patient 300 to contact bodily fluids for example blood, blood plasma, serum, cerebrospinal fluid (CSF), sweat for example on the surface of the skin, and/or saliva in non-limiting examples.

As such the biosensor patch and EIS readings following contact with these fluids may detect changes in a biomarker such as alpha-synuclein (α-Syn) in a patient giving vital information as to disease progression. In an example as illustrated in Table 4, the biosensor may be able to detect as little as a 1% fluctuation in biomarker levels. Table 4 indicates normal αSyn concentrations in various bodily fluids, elevated levels in for instance, Parkinson's Disease (PD) patients, and expected biosensor patch sensitivity in picogram (pg) per milliliter (ml) of fluid.

TABLE 4

| Bodily Fluid | Normal α-Syn Range | PD-Related Elevated Range | Biosensor Patch Detection Sensitivity |
|---|---|---|---|
| Blood Plasma | 10-140 pg/mL | 200-800 pg/mL | ±5 pg/mL |
| Serum | 50-300 pg/mL | 400-1500 pg/mL | ±10 pg/mL |
| Cerebrospinal Fluid (CSF) | 250-1500 pg/mL | 2000-5000 pg/mL | ±20 pg/mL |
| Sweat/Skin Surface Fluid | 1-50 pg/mL | 60-300 pg/mL | ±2 pg/mL |
| Saliva | 5-80 pg/mL | 100-500 pg/mL | ±5 pg/mL |
| Interstitial Fluid | 20-120 pg/mL | 180-600 pg/mL | ±5 pg/mL |

The biosensor differentiates between normal and pathological levels by detecting impedance shifts proportional to biomarker binding. These shifts are mapped, which correlates concentration variations with disease progression and symptom fluctuations. In use, the biosensor patch 200 undergoes initial calibration using a set of standardized α-Syn spiked reference solutions. A real-time adaptive filtering ensures signal clarity, compensating for noise and environmental factors such as sweat composition variations. Real-time adaptive filtering is a signal processing technique applied to the impedance measurements in the biosensor. Real-time filtering reduces noise and account for variations in environmental conditions, such as changes in sweat composition, temperature fluctuations, or external electromagnetic interference. In use, the layered receptor 100 contacts the bodily fluid taking real-time readings of binding events via impedance readings.

The biosensor patch 200 will enable early diagnosis and disease monitoring for Parkinson's Disease allowing continuous α-Syn tracking which enables early PD detection and longitudinal disease progression analysis. Further the biosensor patch 200 could be useful in clinical trials enhancing rates of drug development and testing. The biosensor patch 200 provides a minimally invasive wearable data collection system that may enable personalized treatment adjustments. In some instances, the layered receptor 100 in a conductive needle or wire sits on the skin taking readings from, for instance, sweat collecting biomarker measurements in a non-invasive manner. In other instances, the needle or wire may pierce the skin taking readings from other bodily fluids such as serum, collecting biomarker measurements in a minimally invasive manner. This sampling procedure may be described as microfluidic sampling system.

In other words, the disclosure comprises a method for measuring biomarker levels comprising: configuring a layered receptor comprising: at least one layer comprising graphene oxide, and at least one layer comprising a biomarker binding layer configured to bind with a targeted biomarker; connecting a working electrode comprising carbon nanotubes (CNT) and a reference electrode to the layered receptor; and detecting events comprising the targeted biomarker binding with the biomarker binding layer by measuring changes in impedance to a plurality of frequencies of an alternating current voltage signal applied through a patient's body fluid between the working electrode and the reference electrode. The method for measuring biomarker levels may comprise a method wherein the method further comprises configuring the layered receptor with a plurality of self-assembled layers, comprising, in sequence, a layer abutting the CNT and comprising at least one metal nanoparticle polymer layer, at least one layer comprising an organosulfur, the graphene oxide layer, and the biomarker binding layer. The method may further comprise calibrating the changes in impedance with known biomarker concentrations. The method for measuring biomarker levels may comprise a method wherein the polymer in the metal nanoparticle polymer layer comprises a biocompatible polymer. The method may comprise a method wherein the polymer in the metal nanoparticle polymer layer is selected from monemethylamine (MMA), dimethylamine (DMA), trimethylamine (TMA), methylamine hydrochloride, and 1-pyrene-methylamine (PMA). The method may comprise a method wherein the polymer in the metal nanoparticle polymer layer is PMA. The method may comprise a method wherein the metal nanoparticles comprise gold. The method may comprise a method wherein the metal nanoparticles comprise silver. The method may comprise a method wherein the organosulfur is selected from a thiol, disulfide, thiol-functionalized polymer, thioether, and dithiocaryolxylate. The method may comprise a method wherein the organosulfur is cysteamine. The method may comprise a method wherein the method further comprises configuring the biomarker binding layer with an antibody, or antibody fragment thereof, wherein the antibody, or antibody fragment is at least 60% similar to at least one of SEQ ID. NOs. 1-4. The method may comprise a method wherein the method further comprises configuring the antibody layer with an antibody, or antibody fragment thereof, wherein a binding region of the antibody, or antibody fragment thereof, is at least 70% similar to at least one of SEQ ID. NOs. 1-4. The method may comprise a method wherein the method further comprises configuring the antibody layer with an antibody, or antibody fragment thereof, wherein a binding region of the antibody, or antibody fragment thereof, is at least 90% similar to at least one of SEQ ID. NOs. 1-4.

The disclosure comprises a biosensor comprising: a layered receptor comprising: a polymer and metal nanoparticle layer, a cysteamine layer, a graphene oxide layer, and an antibody layer; wherein each layer is assembled in a self-assembling fashion the cysteamine layer being added to the polymer and metal nanoparticle layer, the graphene oxide layer being added to the cysteamine layer, and the antibody layer being added to the graphene oxide layer. The biosensor may further comprise a working electrode and a reference electrode. The biosensor may further comprise a counter electrode. The biosensor may comprise a biosensor wherein one or more of the electrodes are a carbon nano tube. The biosensor may comprise a biosensor wherein one or both of the working electrode and the reference electrode is a carbon nano tube. The biosensor may further comprise a sampling apparatus. The biosensor may comprise a biosensor wherein the polymer comprises 1-pyrene-methylamine (PMA), the metal nanoparticle is chosen from a group of gold and silver, and the antibody is an antibody, or antibody fragment thereof, that binds alpha-synuclein.

Although various features have been described with reference to the Drawings, other features are possible. For example, an exemplary implementation in accordance with the present disclosure may be configured to provide real-time measurements of other neurodegenerative diseases based on specific biomarkers. This facilitation may be enabled by changing the biomarker binding layer to target specific proteins that are associated with certain diseases. For each neurodegenerative disease listed in the examples below, targeting these biomarkers with the specified antibodies allows for the specific detection and monitoring of disease progression. Adapting the disclosed techniques to include these biomarkers and antibodies would significantly enhance utility and versatility to diagnose and manage a broad spectrum of neurodegenerative disorders. This approach would require validating the sensor's performance with each new biomarker and antibody pair to ensure specificity, sensitivity, and overall effectiveness.

In the Summary above and in this Detailed Description, and the Claims below, and in the accompanying drawings, reference is made to particular features of various implementations. It is to be understood that the disclosure of particular features of various implementations in this specification is to be interpreted to include all possible combinations of such particular features. For example, where a particular feature is disclosed in the context of a particular aspect or implementation, or a particular claim, that feature can also be used—to the extent possible—in combination with and/or in the context of other particular aspects and implementations, and in an implementation generally.

A number of implementations have been described. Nevertheless, it will be understood that various modifications may be made. For example, the steps of the disclosed techniques may be performed in a different sequence, components of the disclosed systems may be combined in a different manner, or the components may be supplemented with other components. Accordingly, other implementations are contemplated, within the scope of the following claims.

REFERENCE SOURCES

1. Baghallab I, Reyes-Ruiz J M, Abulnaja K, Huwait E, Glabe C. Epitomic Characterization of the Specificity of the Anti-Amyloid Aβ Monoclonal Antibodies 6E10 and 4G8. J Alzheimers Dis. 2018; 66(3):1235-1244. doi: 10.3233/JAD-180582. PMID: 30412489; PMCID: PMC6294585.
2. Baghallab I, Reyes-Ruiz J M, Abulnaja K, Huwait E, Glabe C. Epitomic Characterization of the Specificity of the Anti-Amyloid Aβ Monoclonal Antibodies 6E10 and 4G8. J Alzheimers Dis. 2018; 66(3):1235-1244. doi: 10.3233/JAD-180582. PMID: 30412489; PMCID: PMC6294585.
3. Malia T J, Teplyakov A, Ernst R, Wu S J, Lacy E R, Liu X, Vandermeeren M, Mercken M, Luo J, Sweet R W, Gilliland G L. Epitope mapping and structural basis for the recognition of phosphorylated tau by the anti-tau antibody AT8. Proteins. 2016 April; 84(4):427-34. doi: 10.1002/prot.24988. Epub 2016 Feb. 5. PMID: 26800003; PMCID: PMC5067699.
4. Tau Monoclonal Antibody (HT7), Invitrogen™, Mouse Monoclonal Antibody, MN1000 recognizes normal Tau from human and bovine brain and PHF-Tau. No cross reactivity with Tau from rat brain has been observed. The epitope of this antibody has been mapped on human Tau between residue 159 and 163 (numbering according to human Tau40), corresponding to the amino acid sequence PPGQK.
5. alpha Synuclein Monoclonal Antibody (Syn 211), Invitrogen, Recombinant human alpha-synuclein, Monoclonal, Mouse/IgG1, kappa

SEQUENCE LISTING

```
Sequence total quantity: 5
SEQ ID NO: 1          moltype = AA  length = 115
FEATURE               Location/Qualifiers
```

-continued

```
source                1..115
                      mol_type = protein
                      note = mouse monoclonal antibody raised human sequence
                      organism = unidentified
SEQUENCE: 1
XVQLLESGGG LVOPGGSLRL SCAASGFTFS SYAMSWVRQA PGKGLEWVSA ISGSGGDTYY  60
ADSVXGRFTI SRDNSKNTLY LQMNSLRAED TAVYYCARGY GMDVWGQGTT VTVSS       115

SEQ ID NO: 2          moltype = AA  length = 440
FEATURE               Location/Qualifiers
source                1..440
                      mol_type = protein
                      note = mouse monoclonal antibody raised human sequence
                      organism = unidentified
SEQUENCE: 2
XVQLLESGGG LVQPGGSLRL SCAASGFTFS SYAMSWVRQA PGKGLEWVSA ISGSGGDTYY  60
ADSVXGRFTI SRDNSKNTLY LQMNSLRAED TAVYYCARGY GMDVWGQGTT VTVSSASTKG  120
PSVFPLAPCS RSTSESTAAL GCLVKDYFPE PVTVSWNSGA LTSGVHTFPA VLQSSGLYSL  180
SSVVTVPSSS LGTKTYTCNV DHKPSNTKVD KRVESKYGPP CPPCPAPEAA GGPSVFLFPP  240
KPKDTLMISR TPEVTCVVVD VSQEDPEVQF NWYVDGVEVH NAKTKPREEQ FNSTYRVVSV  300
LTVLHQDWLN GKEYKCKVSN KGLPSSIEKT ISKAKGQPRE PQVYTLPPSQ EEMTKNQVSL  360
TCLVKGFYPS DIAVEWESNG QPENNYKTTP PVLDSDGSFF LYSRLTVDKS RWEGNVFSCS  420
VMHEALHNHY TOKSLSLSLX                                              440

SEQ ID NO: 3          moltype = AA  length = 112
FEATURE               Location/Qualifiers
source                1..112
                      mol_type = protein
                      note = mouse monoclonal antibody raised human sequence
                      organism = unidentified
SEQUENCE: 3
DVVMTQSPLS LPVTLGQPAS ISCRSSQXLV HSDGNTYLMW FQQRPGQSPR RLIYKVSXRN  60
SGVPDRFSGS GSGTDFTLKI SRVEAEDVGV YYCMQGTKQY PTFGQGTKLE IK          112

SEQ ID NO: 4          moltype = AA  length = 54
FEATURE               Location/Qualifiers
source                1..54
                      mol_type = protein
                      note = mouse monoclonal antibody raised human sequence
                      organism = unidentified
SEQUENCE: 4
DVVMTQSPLS LPVTLGQPAS ISCRSSQXLV HSDGNTYLMW FQQRPGQSPR RLIY        54

SEQ ID NO: 5          moltype = AA  length = 5
FEATURE               Location/Qualifiers
source                1..5
                      mol_type = protein
                      note = mouse monoclonal antibody raised human sequence
                      organism = unidentified
SEQUENCE: 5
DNEAY                                                              5
```

What is claimed is:

1. A method for measuring biomarker levels comprising:

configuring a layered receptor with a plurality of self-assembled layers in sequence, wherein the layers consist of in sequence:

(a) a layer with at least one metal nanoparticle and a polymer that abuts a carbon nanotube (CNT) working electrode, (b) a layer with at least one cysteamine layer, (c) at least one graphene oxide layer, and (d) at least one biomarker binding layer configured to bind with a targeted biomarker;

connecting the CNT working electrode and a reference electrode to the layered receptor; and detecting events consisting of the targeted biomarker binding with the biomarker binding layer by measuring changes in impedance of frequencies from 0.5 Hz to 100 kHz of an alternating current voltage signal applied through a patient's body fluid between the working electrode and the reference electrode.

2. The method of claim 1, further comprising calibrating the changes in impedance with known biomarker concentrations.

3. The method of claim 1, wherein the polymer in the metal nanoparticle polymer layer comprises a biocompatible polymer.

4. The method of claim 3, wherein the polymer in the metal nanoparticle polymer layer is selected from at least one of monemethylamine (MMA), dimethylamine (DMA), trimethylamine (TMA), methylamine hydrochloride, and 1-pyrene-methylamine (PMA).

5. The method of claim 4, wherein the polymer in the metal nanoparticle polymer layer is PMA.

6. The method of claim 3, wherein the metal nanoparticle comprises gold.

7. The method of claim 3, wherein the metal nanoparticle comprises silver.

8. The method of claim 1, wherein the method further comprises configuring the biomarker binding layer with an antibody, or antibody fragment thereof, wherein the antibody, or antibody fragment is at least 60% similar to at least one of SEQ ID. NOs. 1-4.

9. The method of claim 1, wherein the method further comprises configuring the antibody layer with an antibody, or antibody fragment thereof, wherein a binding region of the antibody, or antibody fragment thereof, is at least 70% similar to at least one of SEQ ID. NOs. 1-4.

10. The method of claim 1, wherein the method further comprises configuring the antibody layer with an antibody, or antibody fragment thereof, wherein a binding region of the antibody, or antibody fragment thereof, is at least 90% similar to at least one of SEQ ID. NOs. 1-4.

11. A biosensor comprising:

a carbon nanotube (CNT) working electrode, and a layered receptor with a plurality of self-assembled layers in sequence, wherein the layers in sequence consist of:

a polymer and metal nanoparticle layer that abuts the CNT working electrode, a cysteamine layer, a graphene oxide layer, and an antibody layer.

12. The biosensor of claim 11, further comprising a reference electrode.

13. The biosensor of claim 12, further comprising a counter electrode.

14. The biosensor of claim 13, wherein one or more of the reference electrode or counter electrode are a carbon nano tube.

15. The biosensor of claim 12, wherein both of the working electrode and the reference electrode is a carbon nano tube.

16. The biosensor of claim 12, further comprising a sampling apparatus.

17. The biosensor of claim 11, wherein the polymer comprises 1-pyrene-methylamine (PMA), the metal nanoparticle is chosen from a group of gold and silver, and the antibody is an antibody, or antibody fragment thereof, that binds alpha-synuclein.

* * * * *